(12) United States Patent
Kamegawa (10) Patent No.: US 7,016,465 B2
(45) Date of Patent: Mar. 21, 2006

(54) X-RAY CT APPARATUS

(75) Inventor: Masayuki Kamegawa, Nara (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 11/122,644

(22) Filed: May 5, 2005

(65) Prior Publication Data

US 2005/0254619 A1 Nov. 17, 2005

(30) Foreign Application Priority Data

May 14, 2004 (JP) ............................. 2004-145320
Aug. 30, 2004 (JP) ............................. 2004-249821

(51) Int. Cl.
*A61B 6/08* (2006.01)
*A61B 6/00* (2006.01)

(52) U.S. Cl. .............................. 378/63; 378/4; 378/19
(58) Field of Classification Search ................... 378/4, 378/19, 22, 45, 62, 63, 79, 195, 208, 206, 378/98.5; 600/407; 128/920; 382/131
See application file for complete search history.

(56) References Cited

U.S. PATENT DOCUMENTS

| | | | | |
|---|---|---|---|---|
| 4,472,822 A | * | 9/1984 | Swift | 378/10 |
| 5,023,895 A | * | 6/1991 | McCroskey et al. | 378/4 |
| 5,384,861 A | * | 1/1995 | Mattson et al. | 382/131 |
| 5,590,170 A | * | 12/1996 | Zweig | 378/63 |
| 5,678,546 A | * | 10/1997 | Truppe | 600/426 |
| 6,272,204 B1 | * | 8/2001 | Amtower et al. | 378/63 |
| 6,473,489 B1 | * | 10/2002 | Bani-Hashemi et al. | 378/63 |
| 6,574,296 B1 | * | 6/2003 | Stierstorfer | 378/15 |
| 2003/0082104 A1 | * | 5/2003 | Mertelmeier | 424/9.4 |
| 2003/0215051 A1 | * | 11/2003 | Suzuki | 378/19 |
| 2004/0215071 A1 | * | 10/2004 | Frank et al. | 600/407 |

FOREIGN PATENT DOCUMENTS

JP  2004-117024  4/2004

* cited by examiner

*Primary Examiner*—Edward J. Glick
*Assistant Examiner*—Irakli Kiknadze
(74) *Attorney, Agent, or Firm*—Rankin, Hill, Porter & Clark LLP (57) ABSTRACT

An optical camera for photographing a subject held on a rotary stage is disposed on the rotation axis of the rotary stage. A computer calculates a region where CT imaging is possible around the rotation axis by using information relating to the positional relation of an X-ray source, an X-ray detector and the rotary stage in the direction of the optical axis of an X-ray, and information relating to the size of a light receiving surface of the X-ray detector. The region where CT imaging is possible is displayed being superimposed with a subject image photographed by the optical camera on an displaying unit, whereby the position of the subject at that time point can be easily compared with the region where the X-ray transmission data can be obtained.

8 Claims, 7 Drawing Sheets

X-RAY CT APPARATUS

This application claims foreign priority based on Japanese Patent application No. 2004-145320, filed May 14, 2004, and Japanese Patent application No. 2004-249821, filed Aug. 30, 2004, the contents of which are incorporated herein by reference in its entirety.

BACKGROUND OF THE INVENTION

1. Field of the Invention

The present invention relates to an X-ray CT (Computerized Tomography) apparatus for industrial purpose to obtain a tomogram of an industrial product such as an electronic component so as to investigate the inner defect, inner structure etc. of the industrial product in a non-destructive manner.

2. Description of the Related Art

Figure 11A:
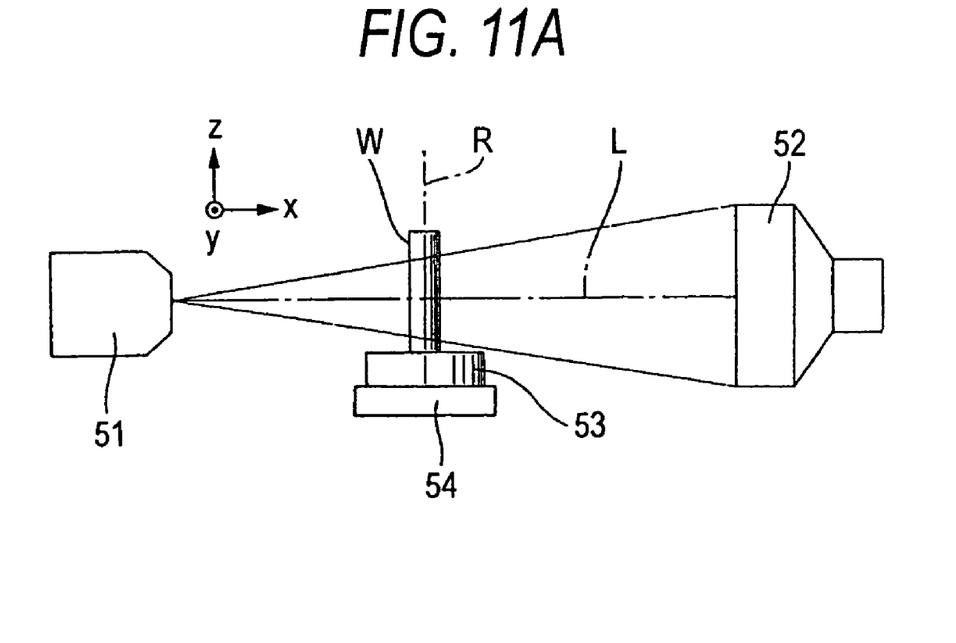
Figure 11B:
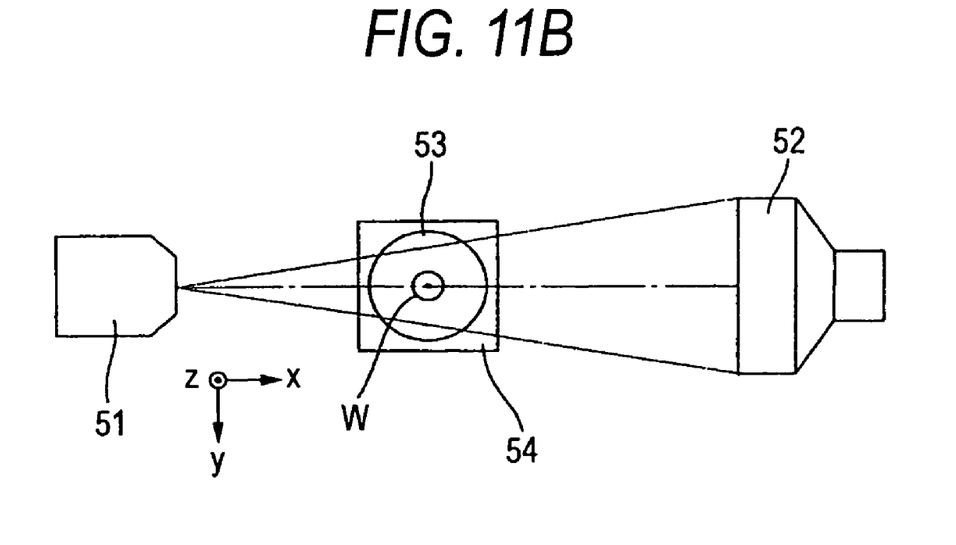

According to the X-ray CT apparatus for industrial purpose, in general, as schematically shown in a front view of FIG. 11A and a plan view of FIG. 11B, a rotary stage 53, which rotates around a rotation axis R that is orthogonal to an optical axis L of an X-ray, is disposed between an X-ray source 51 and an X-ray detector 52. X-ray transmission data is obtained from the X-ray detector 52 for each rotation by a predetermined microscopic angle of the rotary stage 53, while irradiating the X-ray on a subject W in a state of holding the subject on the rotary stage 53. A tomogram of the subject W along a plane orthogonal to the rotation axis R of the rotary stage 53 is reconstructed by using the obtained X-ray transmission data (for example, refer to JP-A-2004-117024). Usually, a moving mechanism 54 can move the rotary stage 53 in a direction along the optical axis L of the X-ray (x-axis direction) and directions of y-axis and z-axis that is orthogonal to the x-axis direction.

Figure 12:
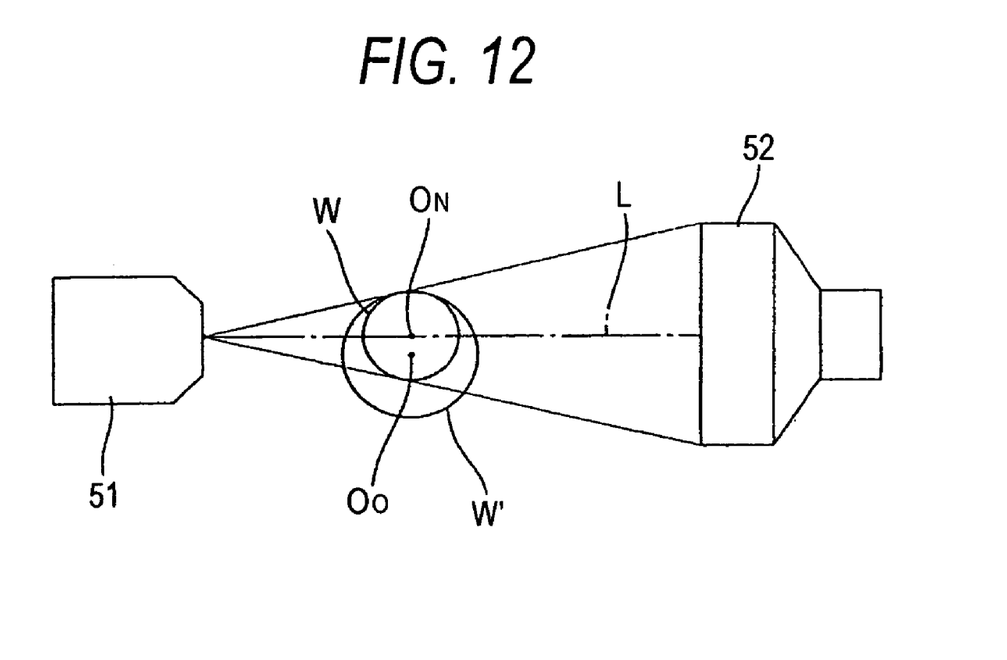
FIG. 12 is a diagram for explaining the obtaining method of X-ray transmission data according to the normal scanning method and the offset scanning method in the X-ray CT apparatus for industrial purpose.

As methods each for obtaining X-ray transmission data so as to obtain a tomogram of a subject by using such an X-ray CT apparatus, as shown by a schematic plan view in FIG. 12, there region normal scan method and an offset scan method. In a normal scan method, the rotation center $O_N$ of a subject W is positioned almost on an optical axis L of an X-ray. In an offset scan method, the rotation center Oo of a subject W' is shifted by a predetermined distance from the optical axis L of the X-ray (for example, refer to JP-A-2004-117024). Although the offset scan method is deteriorated in a SN (Signal to Noise) ratio as compared with the normal scan method, the offset scan method has an advantage that a field angle of CT imaging can be broadened and a tomogram with a high resolution can be obtained.

In the X-ray CT apparatus of the related art, in general, the positioning of a subject and the change of a magnification are performed while looking at the X-ray transparent image of the subject. That is, of course, in order to obtain an intended tomogram, it is necessary to obtain X-ray transmission data of all points on the tomogram. However, in order to obtain an entire tomogram at a predetermined position (height) of a subject, for example, according to the normal scan method, the subject is required to be disposed at such a position that the subject W is entirely irradiated with an X-ray constantly at the height to obtain the tomogram while the subject W makes one revolution, as shown by the subject W in FIG. 12. According to the offset scan method, as shown by the subject W' in FIG. 12, the subject W' is required to be disposed at such a position that there is no region within the subject W' where the X-ray is not irradiated while the subject W' makes one revolution. However, there arise a case where the aforesaid condition can not be satisfied, depending on an imaging magnification based on the positional relation in the x-axis (the optical axis L of the X-ray) direction of the rotary stage 53 and the X-ray detector 52 with respect to the X-ray source 51.

Thus, in the X-ray CT apparatus of the related art, before obtaining the X-ray transmission data of a subject, it is required to place the subject on the rotary stage 53 and rotate the subject by one revolution while irradiating the X-ray on the subject. Further, it is required to confirm whether or not the subject is placed on a position satisfying the aforesaid condition based on X-ray transparent images obtained at respective time points. Further, it is required to change the position of the rotating stage 53 and/or the position of the X-ray detector 52 in the x-axis direction when it is determined that the aforesaid condition is not satisfied. In this manner, the X-ray CT apparatus of the related art has a problem that such a confirmation procedure is troublesome.

SUMMARY OF THE INVENTION

In view of the aforesaid circumstances, an object of the invention is to provide an X-ray CT apparatus in which it is possible to directly figure out an region where X-ray transmission information is obtained, and further, whether or not an intended tomogram can be obtained at the position of a subject at the current time point, without rotating the subject placed on a rotary stage and without obtaining the X-ray transparent image of the subject.

In order to achieve the aforesaid object, the X-ray CT (Computerized Tomography) apparatus according to the invention is an X-ray CT apparatus comprises an X-ray source for irradiating an X-ray on a subject;

an X-ray detector arranged to be opposite to the X-ray source for obtaining an X-ray transmission data of the subject;

a rotary stage holding the subject thereon and rotating around its rotation axis orthogonal to an optical axis of the X-ray, the rotary stage being disposed between the X-ray source and the X-ray detector;

an image reconstruction calculation unit for obtaining a tomogram of the subject along a plane orthogonal to the rotation axis by using the X-ray transmission data of the subject obtained at each rotation of a predetermined angle of the rotary stage while rotating the rotary stage;

an optical camera for photographing the subject placed on the rotary stage from a position on the rotation axis of the rotary stage or a position in vicinity of the rotation axis;

a CT imaging region calculation unit for calculating a region where CT imaging is possible around the rotation axis based on information relating to a positional relation of the X-ray source, the X-ray detector and the rotary stage in a direction of the optical axis of the X-ray and information relating to a size of a light receiving surface of the X-ray detector; and a displaying unit for displaying the region calculated by the CT imaging region calculation unit being superimposed with an optical image of the subject photographed by the optical camera.

The invention may employ the configuration that the optical camera is held on the rotary stage.

Preferably, the invention may employ the configuration that the X-ray CT apparatus further comprises an operation unit which changes a size of the region displayed on a screen of the displaying unit, on the screen of the displaying unit, and a controller which automatically changes a position of at least one of the rotary stage and the X-ray detector in the X-ray optical axis direction in association with the changing operation of the operation unit, so that the region on the screen coincides with an actual region where CT imaging is possible.

The invention may employ the configuration that the X-ray CT apparatus further comprises a moving stage, placed on the rotary stage and mounting the subject thereon, which moves in the X-ray optical axis direction (x-axis direction) and a direction orthogonal to the X-ray optical axis direction (y-axis direction) and also orthogonal to a direction of the rotation axis, wherein the moving stage is moved by designating a rotation center on the optical image of the subject displayed on a screen of the displaying unit or by moving on the screen the region displayed on the screen of the displaying unit, so that the rotation center designated on the optical image or a center of the moved region is positioned on the rotation axis of the rotary stage.

The invention intends to solve the aforesaid problem by performing a simple geometric calculation based on the positional relation of the X-ray source in the optical axis direction of the X-ray with respect to the rotary stage and the X-ray detector so as to obtain a region (circle) where CT imaging is possible having a rotation axis of the rotary stage as its center, and displaying on the displaying unit the region superimposed with the optical image of the subject on the rotary stage.

That is, according to the invention, the optical camera photographs the subject placed on the rotary stage from the position on the rotation axis of the rotary stage or the position in the vicinity thereof thereby to display the subject thus photographed on the displaying unit. Then, the region where CT imaging is possible having a rotation axis of the rotary stage as its center is displayed being superimposed on the screen. Thus, without displaying the X-ray transparent image of the subject by irradiating the X-ray on the subject on the rotary stage, and further without rotating the rotary stage, it is possible to directly figure out whether or not X-ray transmission data for obtaining an intended tomogram can be obtained, that is, whether or not the position of the subject at the current time point is suitable.

The optical camera for photographing the subject on the rotary stage from the position on the rotational axis is merely required to be at the position on the rotational axis when the subject is photographed. For example, the optical camera may be fixed at an arbitrary position such as an apparatus frame and the rotary stage may be positioned just beneath the optical camera when the subject is photographed. Alternatively, the optical camera may be arranged to be movable and may be positioned on the rotation axis when the subject is photographed. However, according to the invention, when such an arrangement is employed that the optical camera is held on the rotary stage so as to be constantly disposed in alignment with the rotation axis, it is not necessary to move the rotary stage or the optical camera when the subject is photographed. Further, according to the invention, the rotation axis of the rotary stage is not required to be completely in alignment with the optical axis of the optical camera, but the optical camera is merely required to be almost in alignment with the rotation axis, that is, to be in alignment with the rotation axis or in the vicinity of the rotation axis, in comparison with the field angle of the optical camera.

Further, as described above, the region displayed on the displaying unit coincides with the actual region where CT imaging is possible (that is, a region where CT imaging is possible at the time when the subject is photographed by the optical camera). However, according to the invention, the size of the region displayed on the screen of the displaying unit may be changed arbitrarily by an operator, and the position of the rotary stage and/or the X-ray detector in the X-ray optical axis direction may be changed automatically, in association with the changing operation, so that the region on the screen coincides with the actual region where CT imaging is possible. According to such a configuration, for example, when an operator confirms on the screen that, for example, the initial position of the subject is not suitable and not disposed within the region where CT imaging is possible, it is merely required to operate so as to change the size of the region displayed on the screen into a size which covers the subject, whereby the rotary stage and/or the X-ray detector region automatically moves in accordance with the operation. Thus, it is possible to remarkably facilitate the positioning operation of the subject (magnification changing operation).

Further, in the case of obtaining the CT image at the noticed region of the subject, the noticed region is positioned on the rotation center and then the CT imaging or photographing of the subject is performed, whereby a tomogram with a high magnification around the noticed region can be obtained. However, according to the invention, the rotation center is designated on the optical image of the subject displayed on the screen of the displaying unit or the region where CT imaging is possible displayed on the displaying unit is moved. Accordingly, the moving stage provided on the rotary stage and mounting the subject thereon is automatically moved, and the subject is moved automatically so that the rotation center designated on the optical image or the moved center of the region where CT imaging is possible is positioned on the rotation center of the rotary stage. According to such a configuration, the CT imaging procedure of the noticed region on the subject can be facilitated and ensured.

BRIEF DESCRIPTION OF THE DRAWINGS

FIGS. 11A and 11B are schematic diagrams showing an example of the configuration of an X-ray CT apparatus of the related art for industrial purpose, in which FIG. 11A shows a front view and FIG. 11B shows a plan view of the apparatus.

DESCRIPTION OF THE PRFERRED EMBODIMENTS

Hereinafter, an embodiment of the invention will be explained with reference to accompanying drawings.

Figure 1:
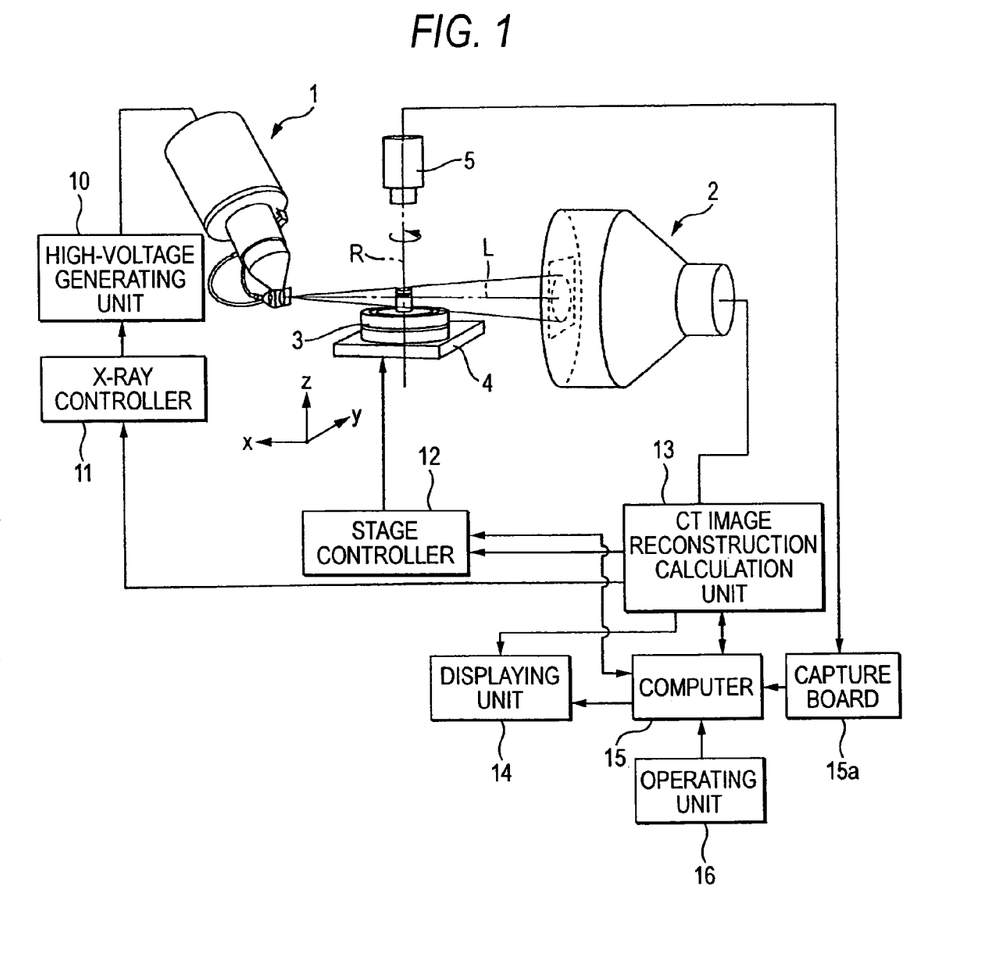
FIG. 1 is a diagram showing the configuration of the embodiment of the invention, in which both a schematic diagram showing the mechanical configuration and a block diagram showing the system configuration of the embodiment are illustrated.

FIG. 1 is a diagram showing the configuration of the embodiment of the invention, in which both a schematic diagram showing the mechanical configuration and a block diagram showing the system configuration of the embodiment are illustrated.

An X-ray detector 2 is disposed in opposite to an X-ray source 1. A rotary stage 3 for mounting a subject W thereon is disposed between the X-ray detector 2 and the X-ray source 1. A rotary stage 3 is arranged to rotate around a rotation axis R extending in a z-axis direction, which is orthogonal to an x-axis direction extending along the optical axis L of an X-ray irradiated from the X-ray source 1. Also, the rotary stage 3 can move in the x-axis, y-axis and z-axis directions which are orthogonal from one another by a stage driving mechanism 4.

The X-ray source 1 generates the X-ray according to a tube voltage and a tube current supplied from a high-voltage generating unit 10. The high-voltage generating unit 10 is controlled by an X-ray controller 11. The rotary stage 3 and the stage driving mechanism 4 are driven and controlled by a driving signal supplied from a stage controller 12, respectively. The X-ray controller 11 and the stage controller 12 are controlled under a CT image reconstruction calculation unit 13 described below.

At the time of CT imaging or photographing, the rotary stage is rotated around the rotation axis R while the X-ray is irradiated on the subject W placed on the rotary stage 3. Then the CT image reconstruction calculation unit 13 reads an X-ray transmission data supplied from the X-ray detector 2 at each rotation of the rotary stage by a microscopic rotation angle. The CT image reconstruction calculation unit 13 constitutes the tomograms of the subject W each sliced along the x-y axis plane orthogonal to the rotation axis R based on the X-ray transmission data of the subject W for 360 degrees supplied from the X-ray detector, and displays the tomograms on a displaying unit 14.

Above the rotary stage 3, an optical camera 5 constituted by a CCD (Charge Coupled Device) camera and a lens is disposed along the rotation axis R so as to be directed vertically downward. The optical camera 5 is coupled to the stage driving mechanism 4 by a column (not shown) etc., whereby the optical camera moves in accordance with the movement of the rotary stage 3 in the x-axis, y-axis or z-axis direction so that the optical camera 5 can be always positioned aligned with the rotation axis R of the rotary stage 3.

Figure 2:
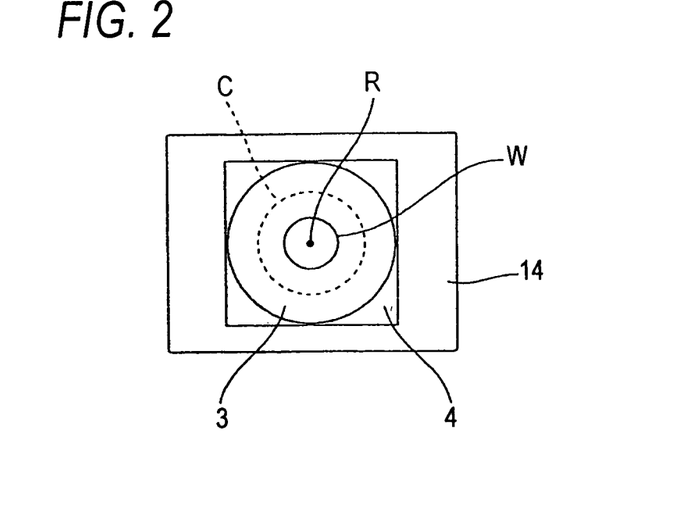
FIG. 2 is an explanatory diagram showing an example of a display of a region where CT imaging is possible in the embodiment of the invention.

An image signal from the optical camera 5, that is, the image signal of the rotary stage 3 and the subject W placed on the rotary stage 3 is sent into a computer 15 through a capture board 15a, and displayed on the displaying unit 14 as an image. The computer 15 is connected to the CT image reconstruction calculation unit 13. The computer 15 calculates a region where CT imaging is possible around the rotation axis R based on the x-axis coordinate and the y-axis coordinate of the rotary stage 3 supplied from the CT image reconstruction calculation unit 13, and displays the region thus calculated superimposed with the image of the subject W on the displaying unit 14. FIG. 2 shows an example of such a display. In FIG. 2, symbols represent corresponding images, respectively. In the figure, a circle C representing the region where CT imaging is possible is displayed being superimposed with the image of the rotary stage 3 and the subject W placed thereon. The center of the circle C coincides with the rotation axis R. An operating unit 16 constituted by a keyboard, a mouse, etc. is connected to the computer 15. The diameter of the circle C representing the region where CT imaging is possible displayed on the displaying unit 14 can be changed arbitrarily by operating the operating unit 16. According to the change of the diameter, the computer 15 automatically moves the stage driving mechanism 4 as described later.

Figure 3:
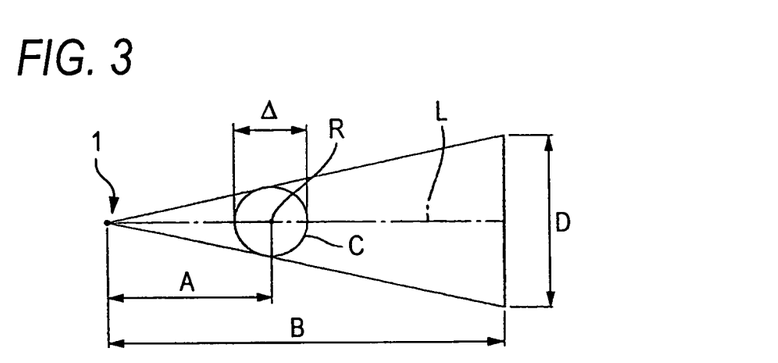
FIG. 3 is a diagram for explaining the calculation method of the size of a circle C representing the region where CT imaging is possible in the case of employing the normal scanning method in the embodiment of the invention.

The size of the circle C representing the region where CT imaging is possible can be calculated according to the geometric calculation described later. FIG. 3 is a diagram for explaining the calculation method in the case of the normal scan method, and FIG. 4 is a diagram for explaining the calculation method in the case of the offset scan method.

In the case of the normal scan method, as shown in FIG. 3, the rotation axis R of the rotary stage 3 is disposed so as to be aligned with the optical axis L of the X-ray. In this case, assuming that a distance in the x-axis direction between the X-ray source 1 (hereinafter also referred as a focal point) and the rotation axis R is A, a distance in the x-axis direction between the X-ray source 1 and the light receiving surface of the X-ray detector 2 is B, and an effective width of the X-ray detector 2 in the y-axis direction is D, the diameter Δ of the circle C representing the region where CT imaging is possible can be represented by the following Expression 1.

$$\Delta = D \times A/B \qquad \text{[Expression 1]}$$

Figure 4:
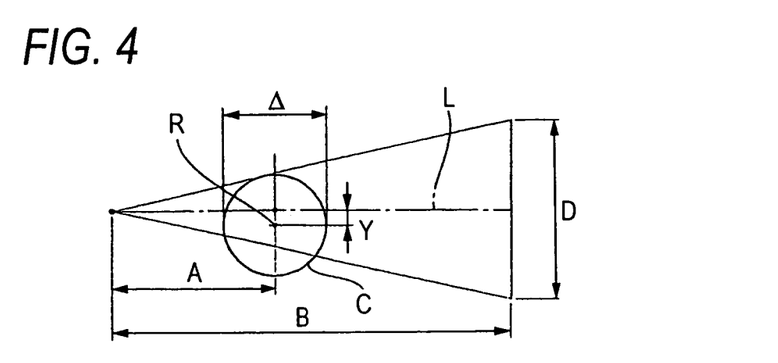
FIG. 4 is a diagram for explaining the calculation method of the size of the circle C representing the region where CT imaging is possible in the case of employing the offset scanning method in the embodiment of the invention.

On the other hand, in the case of the offset scan method, as shown in FIG. 4, the subject W is disposed so that the center of the subject W is shifted by a value Y in the y-axis direction with respect to the rotation axis R. The offset value Y is set as the following Expression 2, for example.

$$Y = 0.8 \times (D/2) \times (A/B) \qquad \text{[Expression 2]}$$

In this case, the diameter Δ of the circle C representing the region where CT imaging is possible can be represented by the following Expression 3.

$$\Delta = D \times A/B + 2Y \qquad \text{[Expression 3]}$$

When the image of the subject W is positioned within the circle C representing the region where CT imaging is possible in any of the normal scan method and the offset scan method, a tomogram sliced at an arbitrary position in the z-axis direction can be obtained. Thus, an operator can directly figure out whether or not the position of the subject W at the current time point is suitable for obtaining an intended tomogram based on the image on the displaying unit 14 as exemplarily shown in FIG. 2.

Then, an operator operates the operating unit 16 to change the diameter of the circle C on the screen of the displaying unit, in the case where the image of the subject W does not exist within the circle C representing the region where CT imaging is possible and so a complete tomogram of the subject W can not be obtained, or in the case where the image of the subject W is too small as compared with the size of the circle C despite that the image of the subject W exists within the circle C and so it is determined that the magnification of the tomogram is small. According to the change of the diameter of the circle C, the actual region where CT imaging is possible at this time point does not coincide with the region surrounded by the circle C. However, since the computer 15 drives the stage driving mechanism 4 to move the rotary stage 3 automatically in the x-axis direction in association with the changing operation of the diameter of the circle C so that the region surrounded by the circle C coincides with the actual region where CT imaging is possible. The moving amount of the rotary stage can be calculated by obtaining the value A which can be obtained by substituting the changed diameter for the diameter Δ of the circle C in the Expressions 1 and 2 while the value B is fixed (set to a constant value).

According to the embodiment, an operator can directly figure out whether or not the position of the rotary stage 3 at the current time point is suitable for obtaining an intended tomogram of the subject W. Further, by merely performing the operation for changing the diameter of the circle C displayed on the screen of the displaying unit 14, the rotary stage 3 can be moved automatically so that the changed circle C coincides with the actual region where CT imaging is possible. Thus, the setting and changing operations can be performed quite easily.

Although the aforesaid embodiment shows an example where the rotary stage 3 is moved in the x-axis direction when the diameter of the circle C is changed, the similar effect of the aforesaid embodiment can be obtained even when the X-ray detector 2 is moved in the x-axis direction or both the rotary stage 3 and the X-ray detector 2 are moved in the x-axis direction.

Further, the aforesaid embodiment is configured in a manner that the optical camera 5 is fixed to the stage driving mechanism 4, whereby the optical camera 5 also moves in accordance with the movement of the stage driving mechanism 4 and so the optical camera 5 is always positioned directly above the rotation axis R of the rotary stage 3. Alternatively, the optical camera 5 may be fixed to the frame of the apparatus etc., for example. In this case, at the time of photographing the subject W to obtain the optical image thereof, the stage driving mechanism 4 is driven to position the rotation axis R of the rotary stage 3 so as to be aligned with the optical axis of the optical camera 5. Then the subject W is photographed to obtain an optical image thereof, the optical image of the subject W is stored in a memory, and the rotary stage 3 is moved and disposed at a position capable of photographing the CT image by driving the stage driving mechanism 4. The displaying unit 14 may display only the image of the subject stored in the memory. Alternatively, the invention may be configured that a mechanism for moving the optical camera 5 in the x-axis and y-axis directions is provided so that the optical camera 5 is moved to be aligned with the rotation axis R of the rotary stage 3 at the time of photographing the subject W to obtain the optical image thereof. Further, in the aforesaid embodiment, although the optical camera 5 is disposed so as to be aligned with the rotation axis R, the center of the visual field of the optical camera 5 is not required to coincide completely with the rotation axis R, but it is sufficient as long as the center of the visual field of the CCD camera coincides almost with the rotation axis R. In this case, although the rotation axis R deviates from the center of the image photographed by the optical camera 5, when the position of the rotation axis R on the image is known, the effect quite similar with the aforesaid case can be obtained by displaying the circle C having the position of the rotation axis R as its center being superimposed with the image photographed by the optical camera 5.

Figure 5:
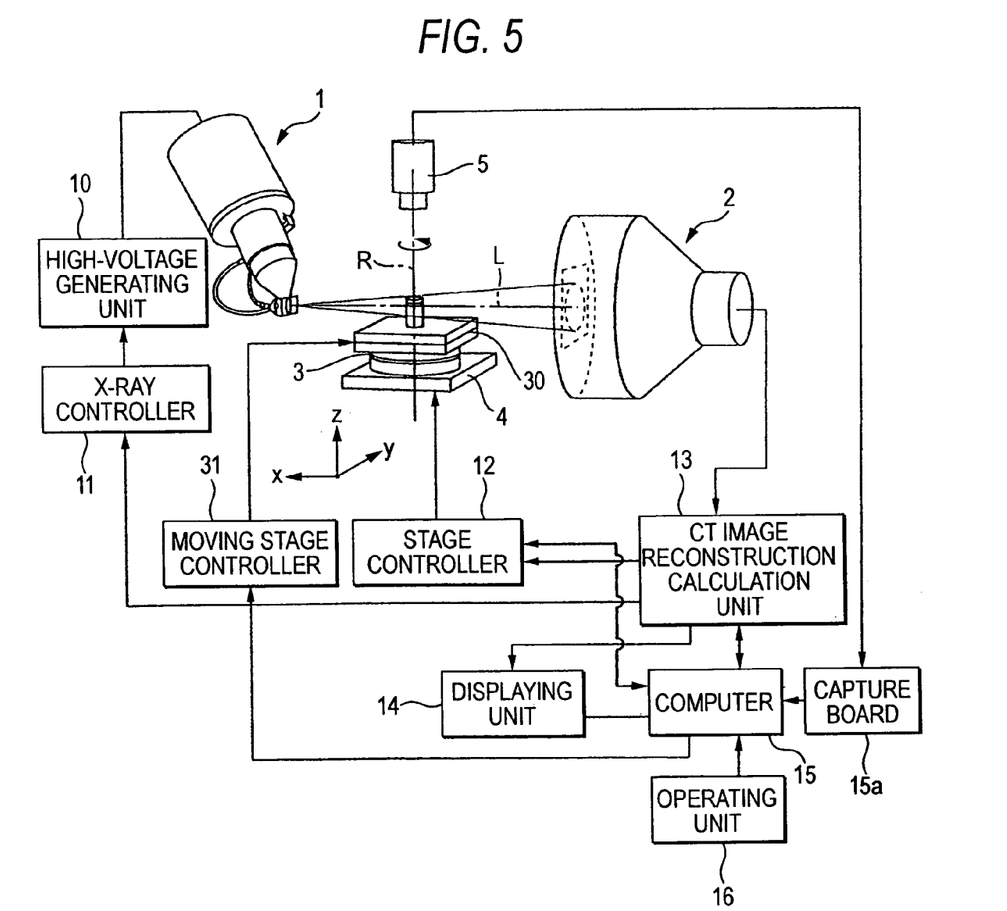
FIG. 5 is a diagram showing the configuration of another embodiment of the invention, in which both a schematic diagram showing the mechanical configuration and a block diagram showing the system configuration of the embodiment are illustrated.

Next, another embodiment of the invention will be explained. FIG. 5 is a diagram showing the configuration of this embodiment, in which both a schematic diagram showing the mechanical configuration and a block diagram showing the system configuration of the embodiment are illustrated.

The features of this embodiment are that a moving stage 30, which mounts the subject W thereon and moves the subject W in the x-axis and y-axis direction, is provided on the rotary stage 3, and that a moving stage controller 31 for driving the moving stage 30 automatically is provided. Other configuration of this embodiment except for these features is same as the aforesaid embodiment and hence the detailed explanation thereof is omitted.

The moving stage 30 on the rotary stage 3 is driven and controlled by a driving signal from the moving stage controller 31. The moving stage controller 31 is under the control of the computer 15. The computer 15 automatically moves the moving stage 30 through the moving stage controller 31 in accordance with the designation of the rotation center by an operator as described bellow.

Figure 6:
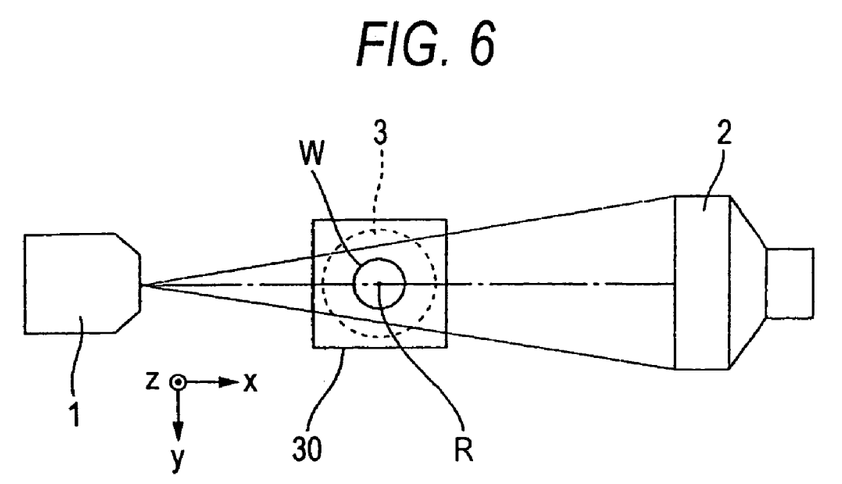
FIG. 6 is a diagram for explaining the operation of the embodiment of FIG. 5, and showing a schematic plan view representing an initial arrangement state of an X-ray source 1, an X-ray detector 2, a rotary stage 3 and a moving stage 30.
Figure 7:
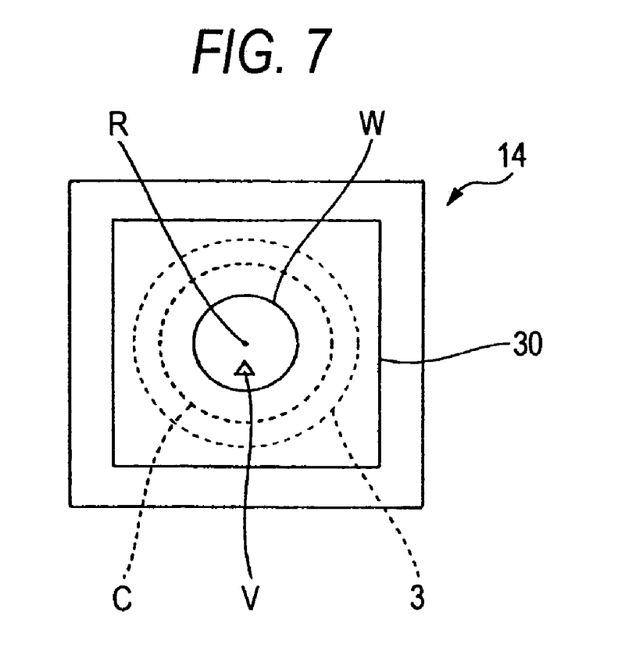
FIG. 7 is an explanatory diagram showing an example of a display of an displaying unit 14 in the state of FIG. 6.
Figure 8:
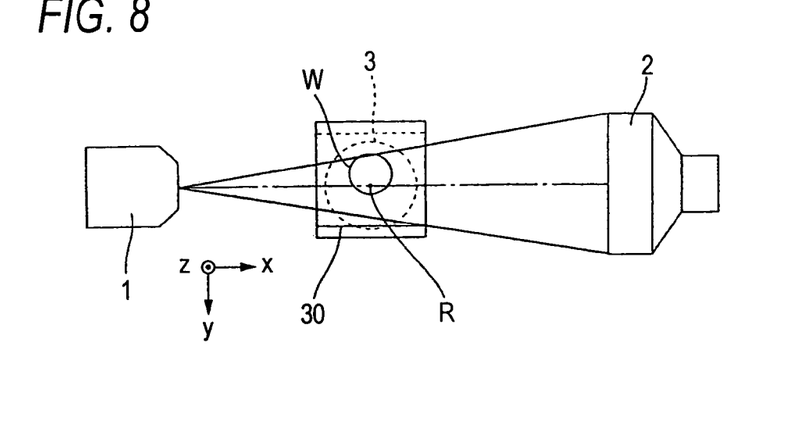
FIG. 8 is a diagram for explaining the operation of the embodiment of FIG. 5, and showing a schematic plan view representing an arrangement state of the respective portions after the moving stage 30 is moved by designating the rotation center on the screen of the displaying unit 14 of FIG. 7.
Figure 9:
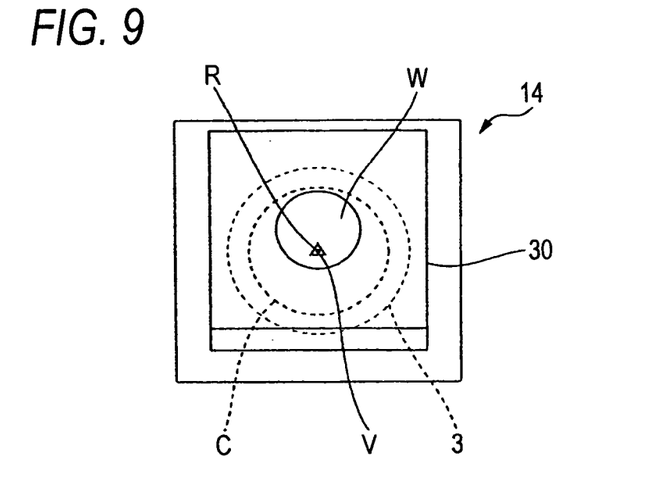
FIG. 9 is an explanatory diagram showing an example of a display of the displaying unit 14 in the state of FIG. 8.

That is, when the X-ray source 1, the X-ray detector 2, the rotary stage 3 and the moving stage 30 are disposed as shown in a schematic plan view in FIG. 6, an image extemporarily shown in FIG. 7 is displayed on the displaying unit 14. In this case, when it is desired to obtain a tomogram of a noticed region V of the subject W with a magnification larger than that set at the current time, an operator operates a mouse, etc. of the operating unit 16 to click the noticed region V on the screen of the displaying unit 14 thereby to designate the rotation center. According to the designation, the computer 15 sends a command to the moving stage controller 31 thereby to move the moving stage 30 automatically, so that the position designated on the screen is disposed being aligned with the rotation axis R of the rotary stage 3. This state is shown in FIG. 8. The screen of the displaying unit 14 in this state is shown in FIG. 9.

Figure 10:
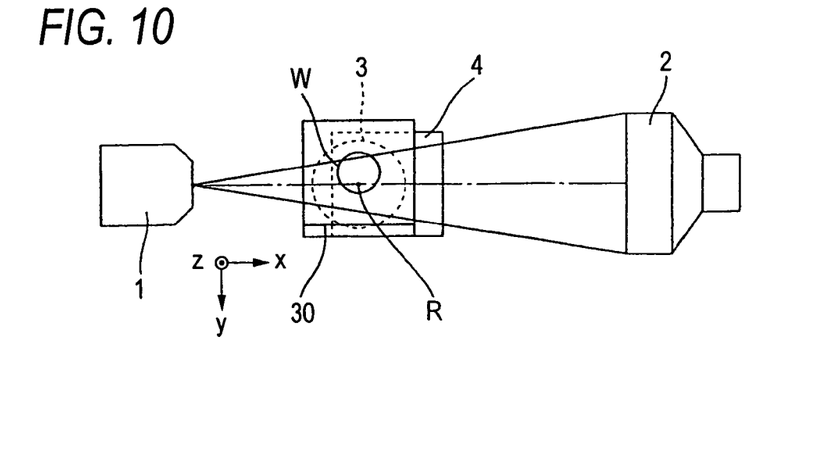
FIG. 10 is a schematic plan view showing an arrangement state of the respective portions after the rotary stage 3 is moved by the stage driving mechanism 4 by changing the diameter of a circle C on the display screen of FIG. 9.

Next, the photographing magnification of the noticed region is changed to a desired value by changing the photographing magnification automatically, based on the change of the diameter of the circle C representing the region where CT imaging is possible. In this case, by making the diameter of the circle C small, the computer 15 drives and controls the stage driving mechanism 4 through the stage controller 12, thereby to move the rotary stage 3 in the x-axis direction and in the direction of approaching to the X-ray source 1 as extemporarily shown in FIG. 10. When the CT imaging is performed in this state, a tomogram with a large magnification around the noticed region V can be obtained. Thus, an operator only operates a mouse, etc. sensuously on the screen of the displaying unit 14, and then the respective mechanisms are driven and controlled automatically to achieve an optimum setting state.

This embodiment shows the example where the rotation center is designated on the screen of the displaying unit 14 when the noticed region V is positioned to be aligned with the rotation axis R. Alternatively, the circle C representing the region where CT imaging is possible displayed on the displaying unit 14 may be dragged by a mouse, etc., moved and positioned at a region surrounding the noticed region V. In this case, the computer 15 gives a command to the moving stage controller 31 so as to move the moving stage 30 so that the center of the moved circle C coincides with the rotation axis R, whereby the effect substantially similar with the aforesaid embodiment can be obtained.

According to the invention, since the region where CT imaging is possible is displayed being superimposed with the optical image of the subject photographed by the optical camera, it can be easily and directly figured out whether or not the subject is placed at the position where the intended CT imaging or photographing can be performed.

Further, according to the invention, the invention may be configured in a manner that the rotary stage and/or the X-ray detector are moved automatically, in association with the operation of changing the size of the region where CT imaging is possible displayed on the screen, so that the changed region coincides with the actual region where CT imaging is possible. Thus, the positioning operation of the subject can be facilitated remarkably.

Further, according to the invention, the invention may be configured in a manner that, by designating the rotation center on the optical image of the subject displayed on the screen, or by moving the region where CT imaging is possible also displayed on the screen, the position of the moving stage is controlled automatically so that the designated rotation center or the center of the moved region where CT imaging is possible is positioned to be aligned with the actual rotation center of the rotary stage. According to such a configuration, the CT imaging procedure of the arbitrary noticed region within the subject can be directly and easily performed.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An X-ray CT apparatus comprising:
   an X-ray source for irradiating an X-ray on a subject;
   an X-ray detector arranged to be opposite to the X-ray source for obtaining an X-ray transmission data of the subject;
   a rotary stage holding the subject thereon and rotating around its rotation axis orthogonal to an optical axis of the X-ray, the rotary stage being disposed between the X-ray source and the X-ray detector;
   an image reconstruction calculation unit for obtaining a tomogram of the subject along a plane orthogonal to the rotation axis by using the X-ray transmission data of the subject obtained at each rotation of a predetermined angle of the rotary stage while rotating the rotary stage;
   an optical camera for photographing the subject placed on the rotary stage from a position on the rotation axis of the rotary stage or a position in vicinity of the rotation axis;
   a CT imaging region calculation unit for calculating a region where CT imaging is possible around the rotation axis based on information relating to a positional relation of the X-ray source, the X-ray detector and the rotary stage in a direction of the optical axis of the X-ray and information relating to a size of a light receiving surface of the X-ray detector; and
   a displaying unit for displaying the region calculated by the CT imaging region calculation unit being superimposed with an optical image of the subject photographed by the optical camera.

2. The X-ray CT apparatus according to claim 1, wherein the optical camera is held on the rotary stage.

3. The X-ray CT apparatus according to claim 2, further comprising:
   an operation unit which changes a size of the region displayed on a screen of the displaying unit, on the screen of the displaying unit; and
   a controller which automatically changes a position of at least one of the rotary stage and the X-ray detector in the X-ray optical axis direction in association with the changing operation of the operation unit, so that the region on the screen coincides with an actual region where CT imaging is possible.

4. The X-ray CT apparatus according to claim 3, further comprising:
   a moving stage, placed on the rotary stage and mounting the subject thereon, which moves in the X-ray optical axis direction and a direction orthogonal to the X-ray optical axis direction and also orthogonal to a direction of the rotation axis,
   wherein the moving stage is moved by designating a rotation center on the optical image of the subject displayed on a screen of the displaying unit or by moving on the screen the region displayed on the screen of the displaying unit, so that the rotation center designated on the optical image or a center of the moved region is positioned on the rotation axis of the rotary stage.

5. The X-ray CT apparatus according to claim 2, further comprising:
   a moving stage, placed on the rotary stage and mounting the subject thereon, which moves in the X-ray optical axis direction and a direction orthogonal to the X-ray optical axis direction and also orthogonal to a direction of the rotation axis,
   wherein the moving stage is moved by designating a rotation center on the optical image of the subject displayed on a screen of the displaying unit or by moving on the screen the region displayed on the screen of the displaying unit, so that the rotation center designated on the optical image or a center of the moved region is positioned on the rotation axis of the rotary stage.

6. The X-ray CT apparatus according to claim 1, further comprising:
   an operation unit which changes a size of the region displayed on a screen of the displaying unit, on the screen of the displaying unit; and
   a controller which automatically changes a position of at least one of the rotary stage and the X-ray detector in the X-ray optical axis direction in association with the changing operation of the operation unit, so that the region on the screen coincides with an actual region where CT imaging is possible.

7. The X-ray CT apparatus according to claim 6, further comprising:
   a moving stage, placed on the rotary stage and mounting the subject thereon, which moves in the X-ray optical axis direction and a direction orthogonal to the X-ray optical axis direction and also orthogonal to a direction of the rotation axis, wherein the moving stage is moved by designating a rotation center on the optical image of the subject displayed on a screen of the displaying unit or by moving on the screen the region displayed on the screen of the displaying unit, so that the rotation center designated on the optical image or a center of the moved region is positioned on the rotation axis of the rotary stage.

8. The X-ray CT apparatus according to claim 1, further comprising:

a moving stage, placed on the rotary stage and mounting the subject thereon, which moves in the X-ray optical axis direction and a direction orthogonal to the X-ray optical axis direction and also orthogonal to a direction of the rotation axis, wherein the moving stage is moved by designating a rotation center on the optical image of the subject displayed on a screen of the displaying unit or by moving on the screen the region displayed on the screen of the displaying unit, so that the rotation center designated on the optical image or a center of the moved region is positioned on the rotation axis of the rotary stage.

* * * * *